United States Patent [19]

Bamforth et al.

[11] 4,169,865

[45] Oct. 2, 1979

[54] PRODUCTION OF AROMATIC HYDROCARBONS

[75] Inventors: John R. Bamforth; Raymond Higgins, both of Middlesbrough, England

[73] Assignee: Imperial Chemical Industries Limited, London, England

[21] Appl. No.: 915,121

[22] Filed: Jun. 13, 1978

[30] Foreign Application Priority Data

Jun. 17, 1977 [GB] United Kingdom ............... 25442/77

[51] Int. Cl.$^2$ .......................... C07C 15/02; B01J 23/08
[52] U.S. Cl. ...................................... 585/314; 252/437; 585/316; 585/321; 585/322; 585/413; 585/418; 585/407; 585/420; 585/508
[58] Field of Search ................ 260/673, 673.5, 677 A, 260/668 R, 668 D, 680 E, 666 A; 252/437

[56] References Cited

U.S. PATENT DOCUMENTS

| | | | |
|---|---|---|---|
| 3,644,550 | 2/1972 | Beuther et al. ...................... | 260/673 |
| 4,036,902 | 7/1977 | Gregory ................................ | 260/673 |
| 4,046,833 | 9/1977 | Hardman ............................ | 260/683.3 |
| 4,056,575 | 11/1977 | Gregory et al. ................. | 260/673 X |
| 4,056,576 | 11/1977 | Gregory et al. ................... | 260/683.3 |
| 4,079,097 | 3/1978 | Antos ................................ | 260/668 D |

*Primary Examiner*—Delbert E. Gantz
*Attorney, Agent, or Firm*—Cushman, Darby & Cushman

[57] ABSTRACT

A process for the dimerization and cyclization of isobutene to form, as preferred product, paraxylene in which the whole of the product of isobutene dimerization (including unreacted feedstock) is contacted with a catalyst for the cyclization of the isobutene dimer. The process is operable in a single dimerization/cyclization stage or in separate dimerization and cyclization stages with no intermediate separation of products. Optionally, the isobutene feedstock is provided by dehydrogenation of isobutane, unreacted isobutane in the resulting feedstock being carried through the dimerization/cyclization and eventually recycled.

14 Claims, No Drawings

PRODUCTION OF AROMATIC HYDROCARBONS

The present invention relates to the dimerisation and cyclisation of olefinic hydrocarbons.

Aromatic hydrocarbons such as benzene, toluene and xylene are commonly produced by the dehydrocyclisation and aromatization (catalytic reforming) of naphthas, followed by extraction with a suitable solvent to separate the aromatic hydrocarbons from the non-aromatic products of the process. The aromatic hydrocarbons are usually separated, one from another, by fraction distillation. This process produces inter alia, a mixture of xylenes and it is usual to separate the xylene isomers by fraction crystallisation and to increase the yield of the more desirable para-xylene by isomerization of the other xylenes. Proposals have also been made for processes for the production of xylenes by dimerisation and cyclisation of olefinic hydrocarbons. Although these processes are by no means unattractive, none of them has yet been found to be sufficiently advantageous to displace catalytic reforming of naphtha as the principal route to the xylene hydrocarbons.

According to the present invention a process for the production of aromatic hydrocarbons comprises contacting a feed comprising isobutene at elevated temperature and in the presence of oxygen with a catalytic amount of a catalyst for the oxidative dimerisation of olefins, to form a product comprising at least one dimer of isobutene and contacting the whole of said product (including any unreacted hydrocarbon feedstock) with a non-acid catalyst for the cyclisation of the isobutene dimer whereby to form a final product comprising aromatic hydrocarbons.

In one embodiment of the process of the present invention the process is operated in two sequential stages viz a first stage in which isobutene is catalytically oxidatively dimerised and a second stage in which the dimer product from the dimerisation stage is catalytically aromatised. In another embodiment, the process can be operated as a single stage process using either a mixed or a dual-function dimerisation/cyclisation catalyst. However, whatever the number of stages used, it is a feature of the process of the invention that the product (and unreacted reactants) of the oxidative dimerisation stage is passed in its entirety, without separation of any of its components, to the cyclisation stage.

In the two-stage embodiment of the process of the invention, the preferred catalyst for the oxidative dimerisation is a metal oxide selected from one or more oxides of metals of Groups II to VIII of the Periodic Table, more preferably oxides of metals of Groups IIB, IIIB, IVB and VB. Bismuth oxide is a particularly preferred catalyst. Optionally, the catalyst may also contain a small amount of a promoter, for example an alkali metal oxide.

The most preferred catalyst for the oxidative dimerisation is bismuth oxide either alone or mixed with one or more oxides. It is desirable that some of the bismuth oxide in the catalyst is present in a reduced state. The amount of reduced bismuth oxide is likely to vary from point to point in the bed. For example, at the upstream end of the catalyst bed there may be no reduced bismuth oxide while at the opposite end the bismuth oxide may be in a very reduced state. Taken over the whole bed, the average degree of reduction should lie in the range of 1 to 70%. Preferably, the average degree of reduction lies in the range 2% to 50%.

We have found that the gas phase oxygen profile throughout the catalyst bed in the oxidative dimerisation stage has a pronounced effect upon the course of this part of the process of the invention. The actual gas phase profile through the oxidative dimerisation catalyst bed depends on the combination and interaction of a number of factors, for example the composition of the feed, the reaction temperature and pressure, and the contact time of the reactant(s) with the feedstock bed. In addition, it is preferred to keep the oxygen concentration at any point in the bed relatively low, preferably at less than 10 vol %, more preferably at less than 5 vol %. To this end, if desired, the oxygen can be fed at several points along the length of the bed. A measure of the degree of oxygen conversion provides a useful guide to the oxygen profile. We have found that very suitable conditions for oxidative dimerisation occur if the degree of oxygen conversion, measured at the downstream end of the catalyst bed, lies in the range 90 to 99%.

In the process of the invention, isobutene is converted to paraxylene, via 2,5 dimethylhexa-1,5-diene as the dimer intermediate. It is preferred, therefore, to select and adjust conditions in the oxidative dimerisation stage as to lead to preferential formation of 2,5-dimethylhexa-1,5-diene. The preferred reaction temperature is in the range 400° to 600° C., more preferably in the range 500° to 575° C. The partial pressure of olefin is preferably in the range 0.20 to 0.99 atmospheres, more preferably greater than 0.55 atmospheres. The partial pressure of oxygen is preferably in the range 0.01 to 0.30 atmospheres, more preferably in the range 0.05 to 0.20 atmospheres. The contact time is preferably within the range 0.05 to 4 seconds, more preferably within the range 0.05 to 1 second. It is preferred to confine the olefin conversion to such a level, for example a maximum of about 20% to 30% as to avoid production of undesirable side-products which might occur at higher conversions. The maintenance of the olefin conversion at a suitable level is readily achieved using process conditions within the preferred ranges outlined hereinbefore and those skilled in this art should find little difficulty in selecting suitable combinations of process conditions.

In the cyclisation (aromatisation) stage of the two-stage form of the process of this invention, the dimer contained in the product of the dimerisation stage is aromatised and in the preferred embodiments of the invention, 2,5-dimethylhexa-1,5-diene, obtained by dimerisation of isobutene, is converted to para-xylene. The catalyst used in the cyclisation stage may be any one of the well known cyclisation/aromatization catalysts, for example chromia-alumina, magnesium oxide, gallium, zinc, germanium, indium, tin, and compounds of these metals provided that the catalyst is substantially non-acidic i.e. it does not isomerise the carbon skeleton. If necessary, the catalyst may be neutralised by addition of a base. The preferred temperature in the cyclisation stage of the process is in the range 300° to 600° C., more preferably, especially in the case in which chromia-alumina is used as catalyst, in the range 500° to 575° C. To avoid problems in separating uncyclised dimer from para-xylene, it is preferred to operate the cyclisation stage at as high a dimer conversion as possible, if possible up to 100%. This is most easily achieved by controlling the contact time of the dimer and it is preferred to operate at a contact time in the range 0.05 to 6 seconds. Those skilled in this art will be able to decide readily what is the optimum contact time for the conditions which they are using.

It is preferred to operate the cyclisation stage of the process in the absence of, or with only a low concentration of, oxygen. We have found that the aromatisation catalyst, for example chromia-alumina, is somewhat susceptible to the presence of oxygen, becoming less selective. Thus it is preferred to operate the dimerisation stage of the process at as high a conversion of oxygen as possible so that no, or only a small amount of, oxygen is carried forward to the second stage.

As hereinbefore described, a further form of the process of this invention involves the use of a bed of dimerisation/cyclisation catalyst. The catalyst may comprise a mixture of the dimerisation catalyst and cyclisation catalyst which can function selectively in the presence of gaseous oxygen for example a mixture of bismuth oxide and chromia-alumina, or may comprise a single dual-function catalyst. It is considered that particularly suitable dual-function catalysts include bismuth phosphate, bismuth-tin-oxygen, bismuth-gallium-oxygen, bismuth-germanium-oxygen and bismuth-zinc-oxygen compositions. Optionally in those cases where bismuth oxide is a compound of the catalyst, the bismuth oxide is suitably present in a partially reduced state. Taken over the whole bed of catalyst, a suitable degree of reduction is in the range 1 to 70%, more suitably 2 to 50%. In this form of the invention, it is necessary to use a rather higher oxygen level, approximately three times more, than the level used in the form of the process using separate dimerisation and cyclisation catalysts. (In a similar way, if hydrogen either from isobutane dehydrogenenation or, in the two-stage embodiment of the process, from the cyclisation stage is combusted over the dimerisation stage, it is necessary to increase the oxygen level over the dimerisation catalyst by about 3 to 5 times). In these conditions, the selectivity of the dimerisation reaction can be maintained by ensuring 90% to 99% oxygen conversion. It is preferred, also, to keep the oxygen concentration at any point in the bed relatively low, preferably at less than 10 vol %, more preferably at less than 5 vol %. To this end if desired, the oxygen can be fed at several points along the length of the bed. The partial pressure of oxygen is preferably in the range 0.01 to 0.30 atmospheres, more preferably in the range 0.05 to 0.20 atmospheres. The partial pressure of olefin is preferably in the range 0.20 to 0.99 atmospheres, more preferably greater than 0.55 atmospheres.

In a further preferred embodiment of the invention which is operable with either the one-or two-stage embodiments hereinbefore described the feedstock comprises isobutane, optionally containing some isobutene. In this preferred embodiment, the isobutane feedstock is subjected to a dehydrogenation stage so as to convert it, at least in part, to isobutene for use in the one- or two-stage embodiment of the process. Typical dehydrogenation catalysts are platinum on alumina and chromia-alumina. The reaction temperature for the dehydrogenation stage is preferably in the range 350° to 650° C., more preferably in the range 500° to 600° C. The preferred range of contact time is 0.5 to 6 seconds.

Unreacted isobutane is preferably separated with unreacted isobutene from the products of the dimerisation/cyclisation stage or cyclisation stage and recycled either to (i) the dehydrogenation stage of the process or to (ii) the dimerisation/cyclisation or dimerisation stage or partially to both (i) and (ii). There is some evidence that coke tends to form on the bed of the dehydrogenation stage and we have found that this undesirable formation of coke can be limited by restricting the amount of unreacted products which are recycled to the dehydrogenation stage. It is preferred to pass at least a portion of the recycle stream to the dimerisation/cyclisation or dimerisation stage.

Following formation of the aromatic product, in both the one- or two-stage embodiments of the process the aromatic product, other organic species and water are separated for example by condensation or by solvent extraction from any unreacted olefin reactant. Paraxylene is then extracted by distillation. Any hydrogen produced in the aromatization stage of the process can also be separated by condensing the unreacted olefin stream. Carbon dioxide can be removed by dissolution in an appropriate solvent, for example potassium carbonate. Preferably, unreacted olefin reactant, for example isobutene, is recycled to the dimerisation/cyclisation stage (one-stage process) or dimerisation stage (two-stage process). If desired, any hydrogen which has not been separated from the products of the process can also be recycled to the dimerisation/cyclisation stage or the dimerisation stage of the process. There it can be oxidised and the heat generated thereby can be used to produce steam and thus reduce the overall service costs of the process.

In the process of the present invention, we have found that the amount of undesired side-products, for example methacrolein is relatively low and although this compound is formed in the dimerisation stage, there appears to be little or no adverse effect on the aromatisation stage of the process. A certain amount of 2,5 dimethyl hexa-2,4-diene may be formed in the cyclisation stage of the process. This dimer is very difficult to separate from the products of the process, for example para-xylene, but we have found that the use of complete (or as nearly complete as possible) conversion of 2,5 dimethyl hexa-1,5-diene in the cyclisation stage avoids the formation of large amounts of 2,5 dimethyl hexa-2,4-diene.

Although the use of a diluent is not ruled out in the process of this invention, it is preferred to operate in the absence of a diluent. However, in some circumstances safety and other considerations may require the use of a diluent in the form of an inert gas, for example nitrogen, carbon dioxide.

The process of this invention is illustrated by way of example in the Examples 1 to 3.

PREPARATION OF CATALYSTS 93 g. of bismuth nitrate pentahydrate were dissolved in 100 ml of concentrated nitric acid and the solution was diluted with 200 ml of distilled water. Concentrated ammonia was added to the solution with constant stirring until no more hydrated bismuth oxide was precipitated. The precipitate was filtered out and the filter cake was carefully dried. The drying temperature of 100° C. was approached from ambient temperature by a series of 20° increments at half-hour intervals and it was maintained at 100° C. for at least 5 hours. The dried catalyst was broken and sieved into 16 to 20 mesh (1.0 to 0.71 mm) particles which were then calcined at 550° C. for at least 10 hours. This temperature was approached from ambient temperature by an increment of 50° C. in the first hour and by a series of 100° C. increments every hour thereafter. The resulting catalyst was shown to be α-bismuth oxide.

The chromia-alumina catalyst used in the Example 1 contained 12.7 wt % chromium and 0.4 wt % sodium and its surface area was 84.8 m²g⁻¹. Before use, the catalyst was broken and sieved, the 10 to 20 mesh (1 to 0.71 mm) particles being used.

EXAMPLE 1

(Two-stage embodiment of the process)

A tubular steel reactor was loaded with 1 cc (2.91 g) of bismuth oxide granules prepared as described. On top of these granules was loaded 2 cc of chromia-alumina catalyst. A stream comprising 96.4 weight % isobutene and 3.6 weight % oxygen was passed through the catalyst beds from bottom to top at 550° C. and at a contact time of 0.19 secs with the bismuth oxide and 0.38 secs with the chormia-alumina without intermediate separation of any product or unreacted isobutene. There was a conversion of isobutene of 4% with 80% selectivity to para-xylene. The para-xylene was 98% pure with respect to other xylenes. Oxygen conversion was 99%. Selectivity to 2,5 dimethyl hexa-2,4-diene was less than 0.5%.

EXAMPLE 2

(One-stage embodiment of the process)

A mixture of bismuth oxide and gallium oxide (Mole ratio Bi:Ga=4:1) was calcined in air at 550° C. and sieved to select particles in the size range 700 to 1000μ. A reactor tube was loaded with 1 cc (2.53 g) of this catalyst. A feed of 10% by volume isobutene, 2.5% by volume oxygen and 87.5% by volume was passed over the catalyst at 550° C. with a contact time of 0.8 sec. After five minutes reaction, the selectivities, as measured from the composition of the exit stream, were 34% to acyclic dimers, 18% to para-xylene, 6% to other aromatics and 41% to carbon oxides for an isobutene conversion of 9% and an oxygen conversion of close to 100%.

EXAMPLE 3

In this exploratory example, the effect of the presence of hydrogen on isobutene dimerisation was studied. A reactor tube was loaded with 1 cc (2.10 g) bismuth oxide. Two runs were made with an isobutene-oxygen feed, the first run being in the absence, and the second run in the presence, of hydrogen. The reactor temperature was 550° C. and the run conditions and results obtained are summarised in Table 1.

TABLE 1

| Run No. | Contact Time (Secs) | Hydrogen % In | Hydrogen % Out | isobutene % In | isobutene % Out | Oxygen % In | Oxygen % Out | Conversion of H₂, % | Conversion isobutene % | Selectivity to 2,5DM-1,5HD* % |
|---|---|---|---|---|---|---|---|---|---|---|
| 1 | 0.3 | 0 | 0 | 31.6 | 28.8 | 2.2 | 0.7 | — | 6 | 83 |
| 2 | 0.3 | 2.0 | 0 | 28.1 | 26.0 | 3.3 | 0.2 | 100 | 6 | 80 |

*2,5DM - 1,5HD is 2,5 dimethyl hexa-1,5-diene

For convenience, neither run was extended beyond the dimerisation stage since it is clear that the isobutene dimer can be formed in the presence of hydrogen and conversion of the dimer to para-xylene could be readily achieved. Indeed, despite the presence of hydrogen, isobutene conversion is unaffected and selectivity to the dimer is only slightly reduced thus indicating that a feed containing hydrogen, either from isobutane dehydrogenation or by recycle from the cyclisation stage, can be readily used in the dimerisation stage.

We claim:

1. A process for the production of aromatic hydrocarbons which comprises contacting a feed comprising isobutene at elevated temperature and in the presence of added oxygen with a catalytic amount of a catalyst for the oxidative dimerisation of olefins, to form a product comprising at least one dimer of isobutene and contacting the whole of said product (including any unreacted hydrocarbon feedstock) with a non-acid catalyst for the cyclisation of the isobutene dimer whereby to form a final product comprising aromatic hydrocarbons.

2. A process as claimed in claim 1 in which the process is operated in two sequential stages comprising a first stage for the oxidative dimerisation of isobutene and a second stage for the catalytic aromatisation of the dimer product from the first, dimerisation, stage.

3. A process as claimed in claim 2 in which the catalyst for the oxidative dimerisation stage is a metal oxide selected from one or more oxides of metals of Group VIII of the Periodic Table.

4. A process as claimed in claim 3 in which the catalyst comprises bismuth oxide which is present in a partially reduced state, the average degree of reduction throughout the whole bed being in the range 1 to 70%.

5. A process as claimed in claim 2 in which the degree of oxygen conversion, measured at the downstream end of the dimerisation catalyst bed is in the range 90 to 99%.

6. A process as claimed in claim 2 in which, in the dimerisation stage, the reaction temperature is in the range 400° to 600° C., the olefin partial pressure is in the range 0.20 to 0.99 atmospheres, and the oxygen partial pressure is in the range 0.01 to 0.30 atmospheres.

7. A process as claimed in claim 2 in which the aromatisation stage is carried out in the presence of a non acid catalyst selected from chromia-alumina, magnesium oxide, gallium, zinc, germanium, indium, tin and compounds of these metals, at a reaction temperature in the range 300° to 600° C. and in the absence of, or with a low concentration, of oxygen.

8. A process as claimed in claim 1 in which the process is operated as a single stage process using either a mixed or a dual-function dimerisation/cyclisation catalyst.

9. A process as claimed in claim 8 in which the catalyst is selected from bismuth phosphate, bismuth-tin-oxygen, bismuth-gallium-oxygen, bismuth-germanium-oxygen, bismuth-zinc-oxygen compositions and a mixture of chromia-alumina and bismuth oxide.

10. A process as claimed in claim 8 in which the catalyst comprises bismuth oxide in a partially reduced state, the average degree of reduction over the whole catalyst bed being in the range 1 to 70%.

11. A process as claimed in claim 8 in which the degree of oxygen conversion is in the range 90 to 99%, the partial pressure of oxygen is in the range of 0.01 to 0.30 atmospheres, and the partial pressure of olefin is in the range 0.20 to 0.99 atmospheres.

12. A process as claimed in claim 1 in which the isobutene feedstock is provided by a feed of isobutane which is subjected to dehydrogenation to convert it, at least in part to isobutene.

13. A process as claimed in claim 12 in which unreacted isobutane is separated with unreacted isobutene from the products of the dimerisation/aromatisation stage (one-stage process and aromatisation stage (two-stage process) and recycled to one or partially to both of (i) the isobutane dehydrogenation stage or (ii) the dimerisation/aromatisation stage or dimerisation stage.

14. A process as claimed in claim 1 in which unreacted isobutene is recycled to the dimerisation/aromatisation stage (one-stage process) or to the dimerisation stage (two-stage process).